(12) United States Patent
Kluger

(10) Patent No.: US 7,534,266 B2
(45) Date of Patent: May 19, 2009

(54) IMPLANT AND INSTRUMENT FOR PLACEMENT AND DISTRACTION OF THE IMPLANT

(75) Inventor: Patrick Kluger, Erbach (DE)

(73) Assignee: Ulrich GmbH & Co. KG, Ulm (DE)

( * ) Notice: Subject to any disclaimer, the term of this patent is extended or adjusted under 35 U.S.C. 154(b) by 603 days.

(21) Appl. No.: 10/854,650

(22) Filed: May 26, 2004

(65) Prior Publication Data

US 2005/0004673 A1    Jan. 6, 2005

(30) Foreign Application Priority Data

May 27, 2003    (DE)    ................. 103 24 319

(51) Int. Cl.
*A61F 2/44*    (2006.01)
*F16B 13/06*    (2006.01)
(52) U.S. Cl. .................. 623/17.11; 411/65; 411/68
(58) Field of Classification Search ............. 623/17.11, 623/17.15, FOR. 17; 411/63–65, 68
See application file for complete search history.

(56) References Cited

U.S. PATENT DOCUMENTS

| 6,183,517 | B1 | 2/2001 | Suddaby |
|---|---|---|---|
| 6,419,705 | B1 | 7/2002 | Erickson |
| 6,454,806 | B1 * | 9/2002 | Cohen et al. ............. 623/17.15 |
| 2002/0022887 | A1 | 2/2002 | Huene |
| 2003/0074063 | A1 | 4/2003 | Gerbec et al. |

FOREIGN PATENT DOCUMENTS

WO    WO 2004/019829    3/2004

* cited by examiner

*Primary Examiner*—David H. Willse
(74) *Attorney, Agent, or Firm*—Collard & Roe, P.C.

(57) ABSTRACT

An implant for intersomatic fusion of two adjacent vertebrae, particularly by an operation that was performed in posterior manner. The implant has a first implant part and a second implant part that is adjustable relative to the former, for the purpose of distraction. The first implant part and the second implant part are structured so that they supplement one another, in a complementary manner, in the non-distracted state, to form a pipe that is divided in the longitudinal direction. Guide surfaces that extend radially in the distraction direction, and rest against one another are formed on the first implant part and the second implant part. The relative position of the guide surfaces is fixed in place. An instrument for the placement and distraction of the implant is also provided.

11 Claims, 9 Drawing Sheets

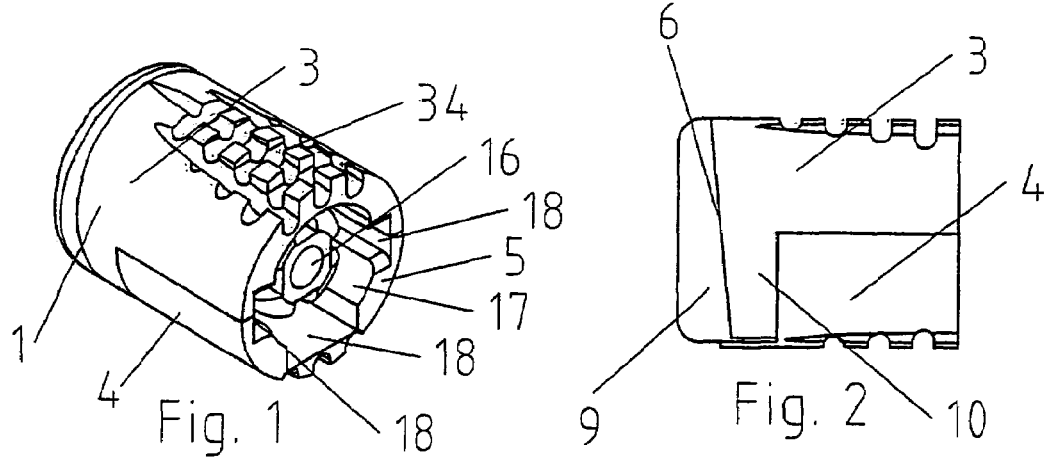
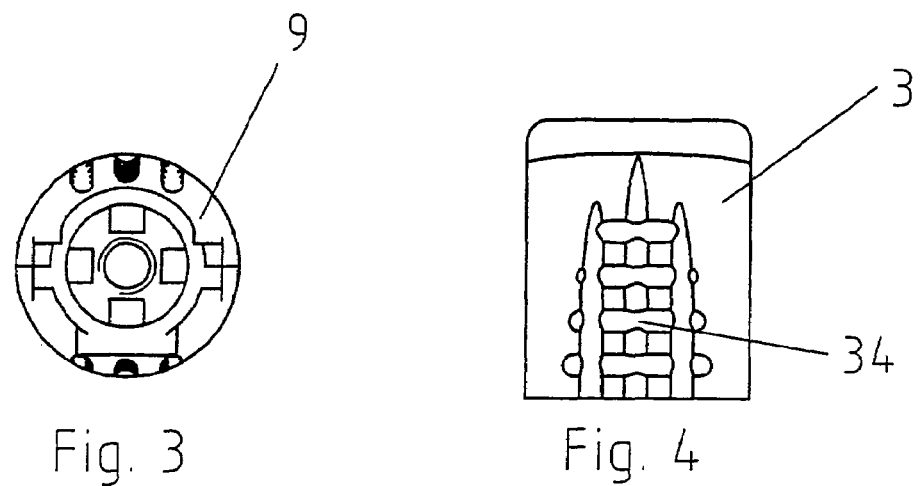
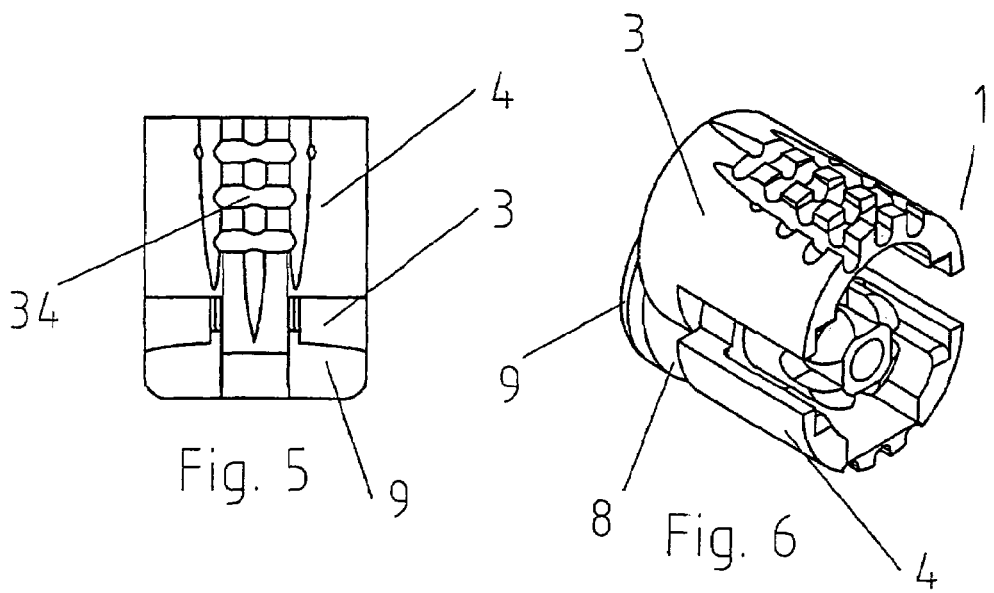

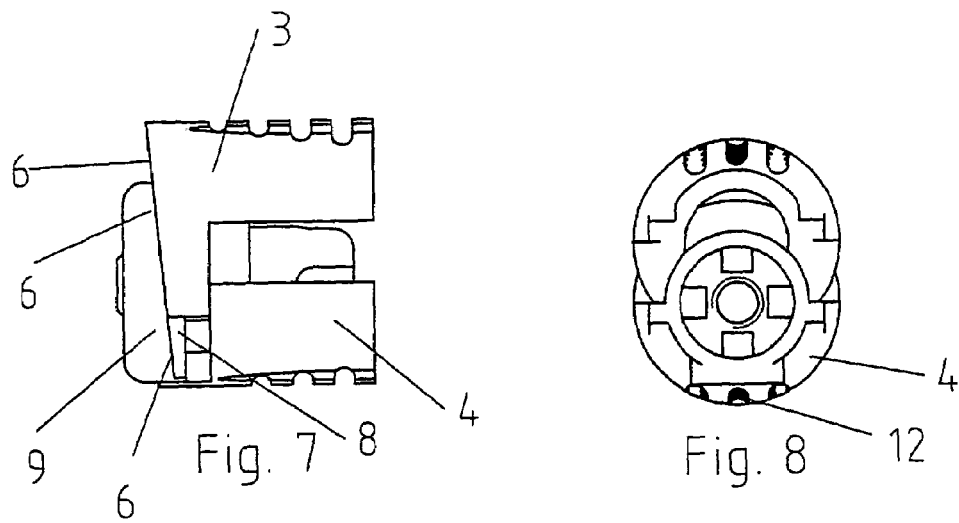
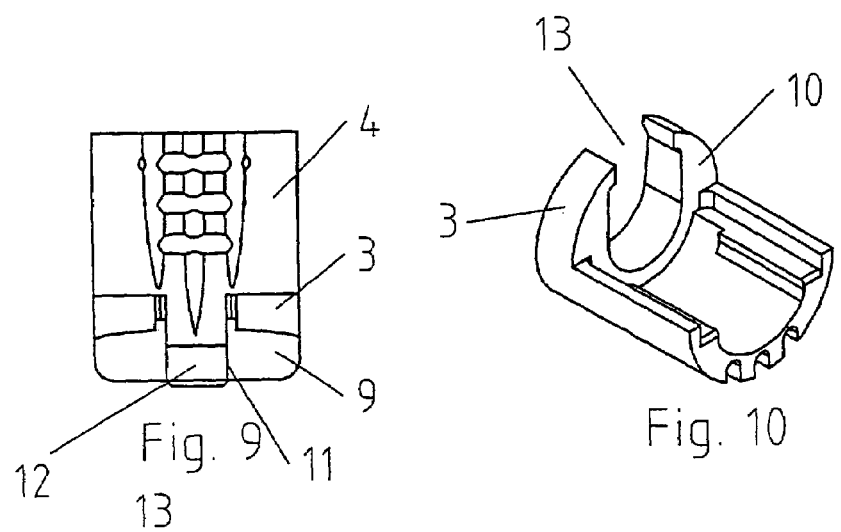
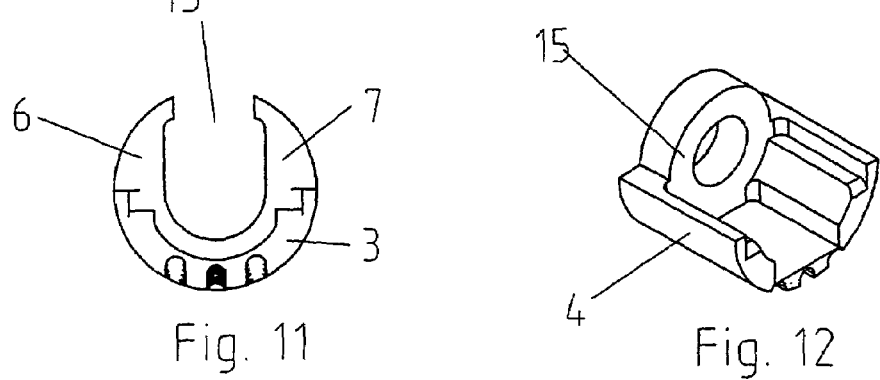

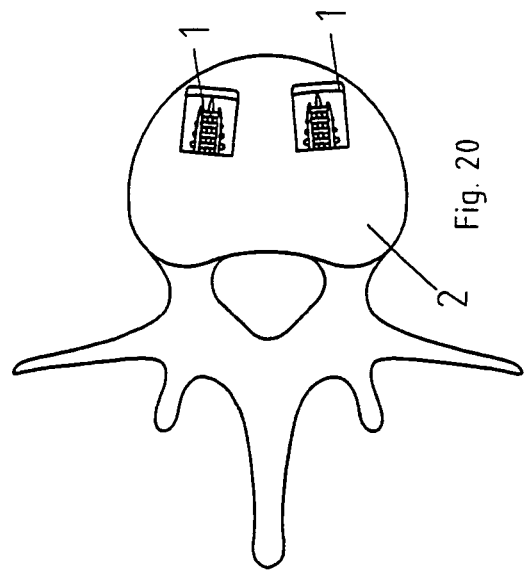
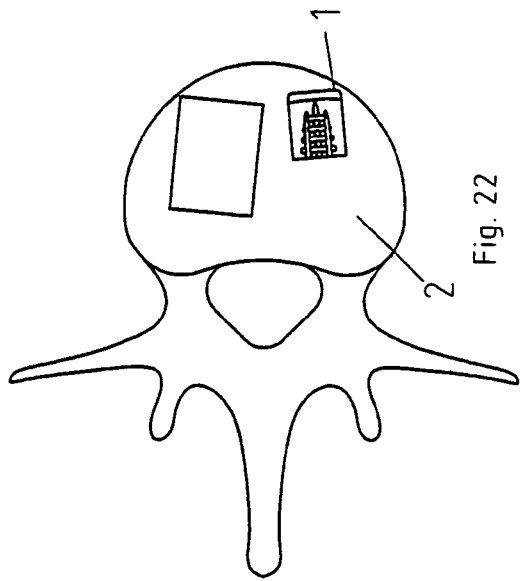
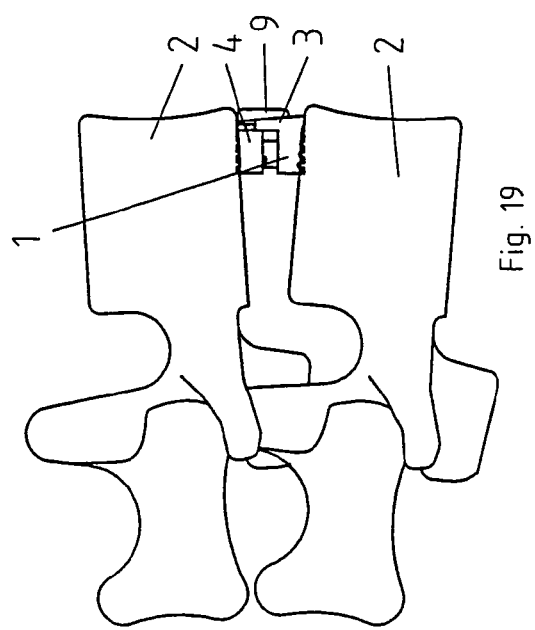
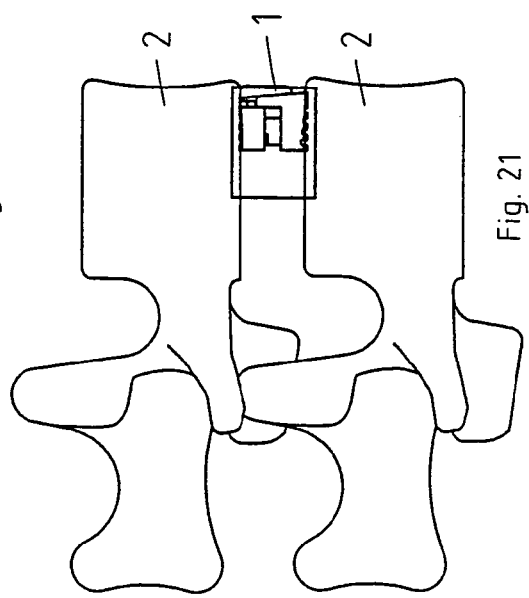

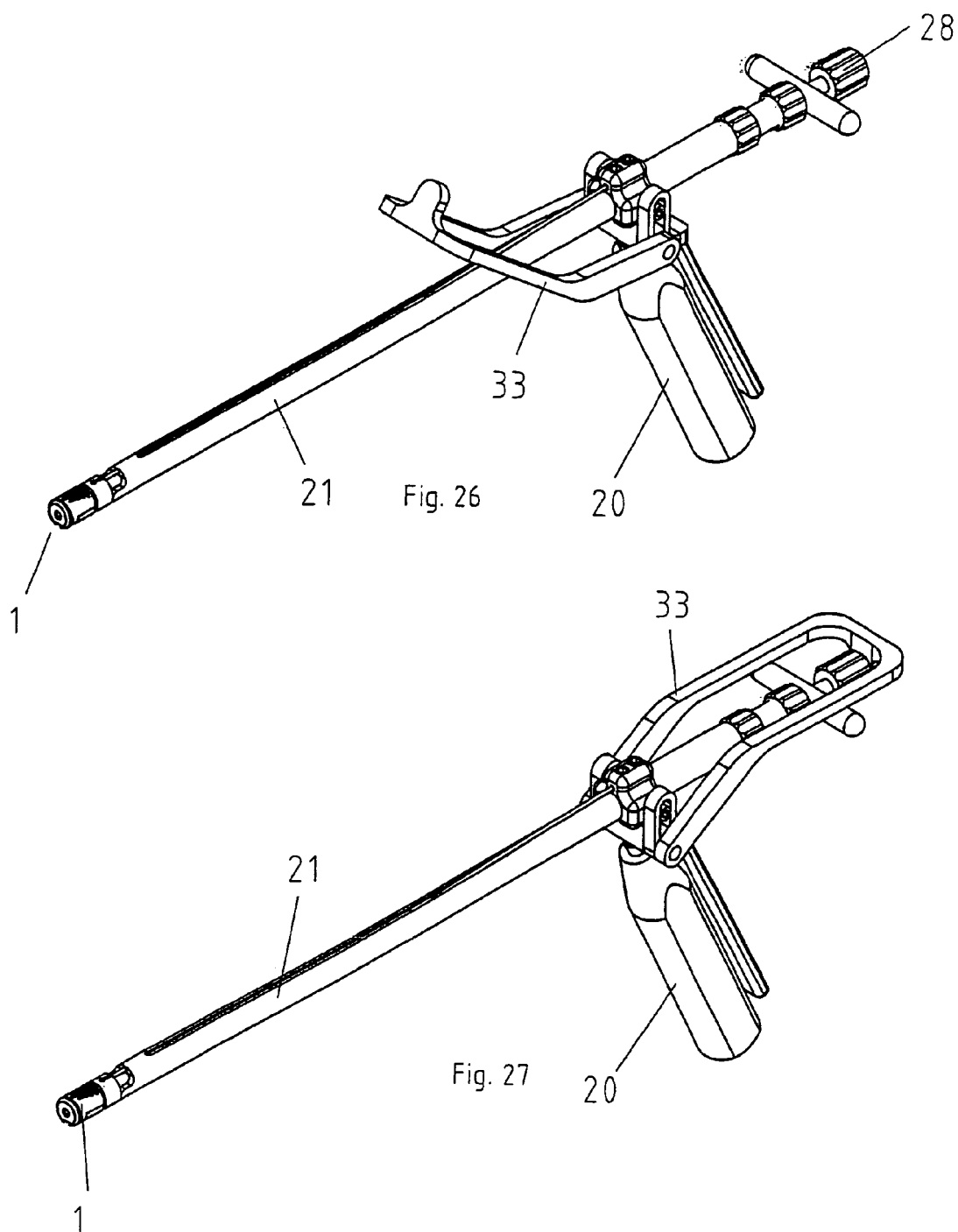

IMPLANT AND INSTRUMENT FOR PLACEMENT AND DISTRACTION OF THE IMPLANT

BACKGROUND OF THE INVENTION

1. Field of the Invention

The invention relates to an implant for intersomatic fusion of two adjacent vertebrae, having a first implant part and a second implant part that is adjustable relative to the former, for the purpose of distraction.

2. The Prior Art

Implants for intersomatic fusion of two vertebrae are used in order to stabilize a segment of the spinal column after the resection of a disk that was considered necessary. In the case of the operating method, a differentiation is made between operating techniques, with regard to access to the spinal column from the back or from the abdominal side, and fundamentally, different general conditions apply for these. In the case of access that takes place from the posterior direction, the spinal cord must be pushed out of the operation region as gently as possible, for the necessary measures for removing the disk, preparing the vertebrae, and inserting the implant to be carried out in the immediate vicinity of the spinal cord, and for the operator to make do with little room.

SUMMARY OF THE INVENTION

It is therefore an object of the invention to develop an implant of the type stated above in such a manner that the construction form can be made smaller, in particular, the length can be reduced, while completely maintaining the distraction possibility and simple operation of the implant for distraction in the operating field, in situ.

In the invention, the first implant part and the second implant part are structured so that they supplement one another, in a complementary manner, in the non-distracted state, to form a pipe that is divided in the longitudinal direction. Guide surfaces that extend radially in the distraction direction and rest against one another are formed on the first implant part and the second implant part. Means are provided for fixing the relative position of the guide surfaces in place.

Such an embodiment of an implant has the advantage that because of the pipe-shaped configuration of the implant in the basic state, as well as the distraction that takes place perpendicular to the pipe axis, a very stable implant that withstands great stress is produced, which can have small dimensions in the distraction direction, in the case of a short but appropriate expanse in the longitudinal direction, so that there is only a small need for space when introducing the implant past the spinal column, between the vertebrae. In this connection, the guide surfaces ensure that a precisely defined movement progression takes place in the adjustment of the two implant parts relative to one another. The guide surfaces are used, at the same time, in order to permanently fix a relative position of the two implant parts in place once it has been achieved. This, in turn, promotes the compact construction form of the implant, since no additional, extensive structures are needed to prevent the two implant parts from becoming incorrectly placed relative to one another.

It has proven to be advantageous if the pipe has a circular cross-sectional shape in the non-distracted state, and forms a cylinder. The cylinder is characterized by its simple geometrical shape, which is easy to produce, and is connected with a great ability to withstand stress.

According to a particularly preferred embodiment of the invention, the guide surface of the first implant part is formed on its face, and that the guide surface of the second implant part is formed in a radially running slit, namely on the inside of a face plate. This achieves the result that the components that are required for the precise adjustment of the two implant parts, as well as for their reciprocal fixation in place, extend radially from the surface of the pipe towards the inside, and therefore no increased need for space is required for these components during insertion of the implant.

The slit preferably widens radially, in the direction of the first implant part. The face plate is preferably formed in two parts with the second implant part and is adjustable in the axial direction. The guide surface of the first implant part is preferably formed on a guide wedge that engages into the slit, having wedge walls that run parallel to the slit walls. By means of this configuration, the relative position of the two implant parts relative to one another can be fixed in place by means of jamming, and can be released again. A reinforcement of the fixation occurs by means of the slit and by means of the guide wedge if the implant is placed under stress, since the guide wedge is pressed into the slit and increases the contact pressure between the guide surfaces with its wedge walls, and thereby increases the frictional engagement.

Since a displacement of the two implant parts relative to one another in the axial direction also occurs during an adjustment of the two implant parts relative to one another in the distraction direction, because of the inclined configuration of the slit walls and the wedge walls, an axially running guide groove is formed in the face plate, for interaction with a guide tab formed on the second implant part. In this way, the axial adjustment of the two implant parts relative to one another also takes place in precisely defined manner.

In order to achieve the greatest possible length of the guide surface, the guide wedge is formed, in the circumference direction, as a ring open on one side, which surrounds the guide tab with its ring opening in the non-distracted state.

With regard to a low need for space, it is advantageous if an axially running threaded bore is formed in the face plate, on the side that faces inward, and a ring eye is formed on the second implant part, to hold a locking screw that engages in the threaded bore, as means for fixing the relative position of the first implant part and the second implant part in place. Fixation of the two implant parts in place can take place simply by turning the locking screw in the threaded bore, or they can be released again, whereby it should be noted that in order to activate the means for fixation, access to the implant merely has to be provided in the axial direction, in other words in the direction in which the space is already available, through which the implant was introduced into its position.

Simple access to the locking screw is achieved in that an implant opening for access into the interior of the implant is formed on the side opposite the face.

A plurality of guide grooves is formed in the implant opening, two of which run along the longitudinal parting between the first implant part and the second implant part. These guide grooves are provided, in this connection, in order to offer the operator an access possibility for adjusting the two implant parts, in precisely defined manner.

If a threaded bore is formed in the free end of the screw head of the locking screw, then there is the possibility of absorbing tensile forces that act on the implant by screwing in a threaded pin, and thereby counteracting a change in the position of the implant, as a whole, during distraction.

Secure anchoring of the implant in the surfaces of the adjacent vertebrae that lie against the implant is promoted in that the surfaces of the pipe that lie opposite one another in the distraction direction have teeth. It is furthermore advantageous if the first implant part and the second implant part are made of surgical steel and/or titanium.

Alternatively or additionally, bone cement that is introduced between the first implant part and the second implant part is also suitable as a means of fixation.

An instrument that is particularly suitable for placement and distraction of the implant comprises a hollow rod connected with a handle, which rod has a pivotable setting element at its front, free end. The element has two pins for insertion into the two guide grooves assigned to the longitudinal parting. On the hollow rod, a sleeve is connected with a pivot lever, which serves for activating a tension piece that engages on the setting element, for pivoting. A hollow screwdriver is arranged in the hollow rod, through which screwdriver a threaded pin to be screwed into the threaded bore of the screw head passes. The implant can be set onto this instrument, in simple manner, in that the pins are inserted into the guide grooves and the screwdriver, together with the threaded pin, is brought into contact with the screw head, in such a manner that the threaded pin is screwed into the threaded bore in order to absorb tensile forces, and the screwdriver rests against the screw head only with a positive lock, in usual manner, in order to be able to exert rotation forces onto the screw. After the locking screw has been loosened, the two guide surfaces of the two implant parts can be displaced relative to one another. The displacement is brought about by operating the pivot lever, which brings about a rotation of the setting element, which produces spreading of the guide grooves perpendicular to the longitudinal parting, with the resulting adjustment of the two implant parts relative to one another. This adjustment, once it has been achieved, can be fixed in place again by activating the locking screw, using the screwdriver.

In order to obtain the greatest possible control during the distraction, it is provided that a rod thread is formed on the back end of the hollow rod, with a threaded ring arranged on it, to limit the setting path of the sleeve.

The tension piece engages at the top end of the setting element. Projections are formed on the hollow rod, in the front region, at the opposite rod walls. These projections define a pivot axis that lies perpendicular to the longitudinal parting of the implant, and the setting element rests against the projections at a distance from its connection with the tension piece. In this manner, the pivot movement of the setting element is introduced with little need for space, by exerting tensile forces on the setting element. These forces are translated into an adjustment of the two implant parts that takes place in the radial direction.

A stirrup is mounted on the handle, which can be pivoted between a position that limits the axial adjustment path of the threaded pin, and a position that eliminates this limitation.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views:

FIG. 1 shows a perspective representation of an implant according to the invention, FIG. 2 shows a side view of the implant from FIG. 1, FIG. 3 shows a front view of the face of the implant from FIG. 1, FIG. 4 shows a top view of the implant from FIG. 1, FIG. 5 shows a representation of the bottom of the implant from FIG. 1, FIG. 6 shows a representation of a distracted implant, corresponding to FIG. 1, FIG. 7 shows a representation of the implant from FIG. 6, corresponding to FIG. 2, FIG. 8 shows a representation of the implant from FIG. 6, corresponding to FIG. 3, FIG. 9 shows a representation of the implant from FIG. 6, corresponding to FIG. 5, FIG. 10 shows a perspective representation of the isolated first implant part, FIG. 11 shows a face view of the first implant part from FIG. 10, FIG. 12 shows a perspective representation of the isolated second implant part, FIG. 19 shows a side view of a distracted implant inserted between two vertebrae, FIG. 20 shows a top view of two implants according to the invention placed on the cover plate of a vertebra, FIG. 21 shows a representation corresponding to FIG. 19, with the need for space for an implant known from the state of the art being indicated, FIG. 22 shows a representation corresponding to FIG. 20, in which the upper implant according to the invention has been replaced by an indication of the space required for an implant known from the state of the art, FIG. 26 shows a perspective representation of the implant set onto the instrument, FIG. 27 shows a representation corresponding to FIG. 26, with the stirrup in the second position.

DETAILED DESCRIPTION OF THE PREFERRED EMBODIMENT

Figure 13:
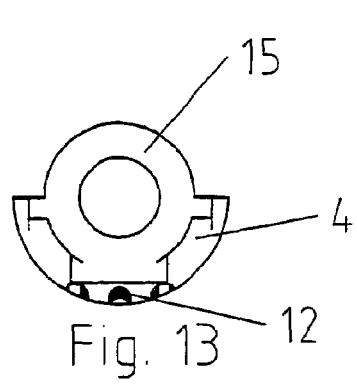
FIG. 13 shows a face view of the second implant part from FIG. 12.
Figure 14:
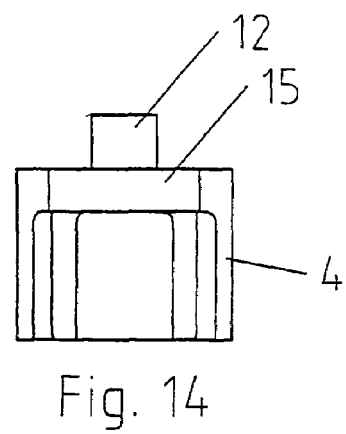
FIG. 14 shows a top view of the second implant part from FIG. 12.
Figure 15:
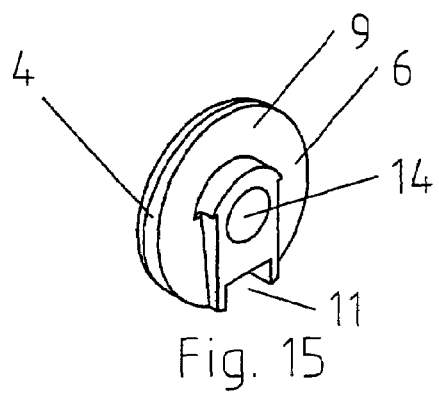
FIG. 15 shows a perspective representation of the isolated face plate.
Figure 16:
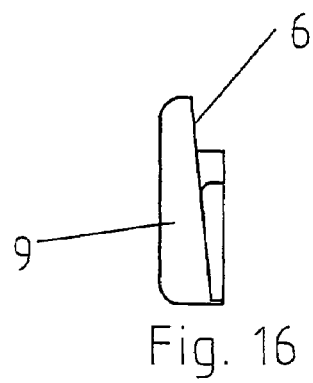
FIG. 16 shows a side view of the face plate from FIG. 15.
Figure 17:
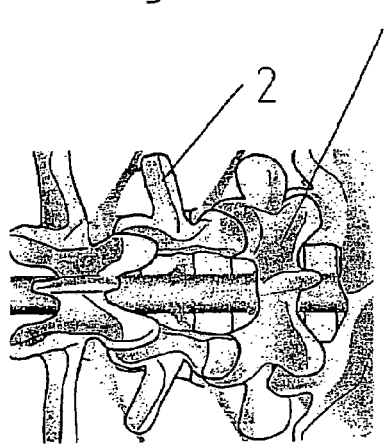
FIG. 17 shows a schematic representation of the spinal column with the spinal cord channel, as it presents itself to the operator after having been exposed, during access from the posterior direction.
Figure 18:
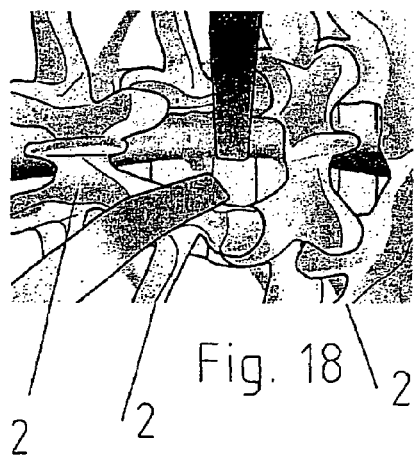
FIG. 18 shows a representation corresponding to FIG. 17, to illustrate the difficulties in creating appropriate space during the operation.

The drawing in FIG. 1 shows an implant 1, which is used for intersomatic fusion of two adjacent vertebrae 2, if access to the spinal column preferably takes place from the posterior direction. Implant 1 consists of a first implant part 3 and a second implant part 4, adjustable relative to the former, for the purpose of distraction. First implant part 3 and second implant part 4 are structured so that they supplement one another, in complementary manner, in the non-distracted state, to form a pipe 5, having a round cross-sectional shape, in other words a cylinder, that is divided in the longitudinal direction. Guide surfaces 6 that extend radially towards the inside, in the distraction direction, and rest against one another, are formed on first implant part 3 and second implant part 4. Guide surface 6 of first implant part 3 is formed on its face 7, and guide surface 6 of second implant part 4 is formed on a radially running slit 8 on the inside of a face plate 9, which is formed in two parts with second implant part 4. Slit 8 widens radially in the direction of first implant part 3; guide surface 6 of first implant part 3 is formed on a guide wedge 10 that engages in slit 8, having wedge walls that run parallel to the slit walls. Face plate 9 has an axially running guide groove 11 that is provided for interaction with a guide tab 12 that is formed on second implant part 4. Guide wedge 10 is structured, in the circumference direction, as a ring open on one side, which surrounds guide tab 12 with ring opening 13 in the non-distracted state.

Implant 1 furthermore possesses way for fixing the relative position of first implant part 3 and second implant part 4 in place, which comprises an axially running threaded bore 14 formed in face plate 9, on the side that faces inward, and a ring eye 15 formed on second implant part 4, whereby ring eye 15 serves to hold a locking screw 16 that engages in threaded bore 14. This locking screw 16 is accessible through an implant opening 17, which is present on a side of implant 1 that lies opposite face 7.

An alternative, not shown in the drawing, uses bone cement as the means for fixation, which is introduced between first implant part 3 and second implant part 4, and fills out and reinforces implant part 1 after it hardens, as a solid core.

Figure 23:
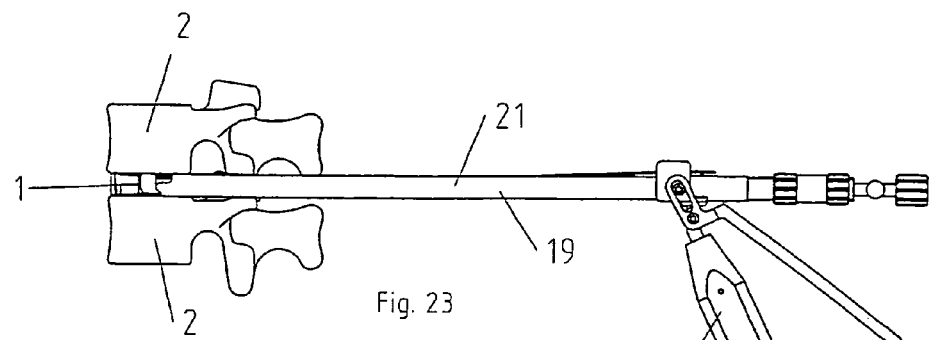
FIG. 23 shows a side view of an implant inserted into the intervertebral space, in the non-distracted state, shown without a stirrup.
Figure 24:
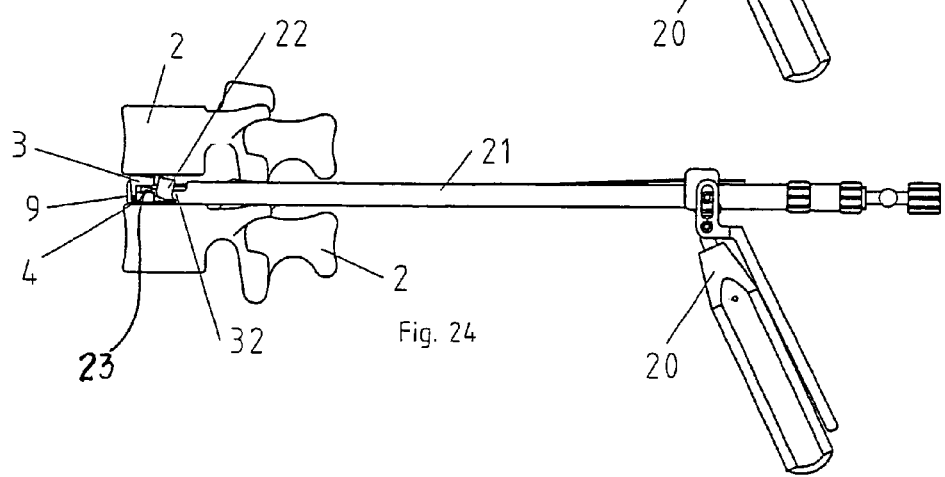
FIG. 24 shows a representation corresponding to FIG. 23, during distraction of the implant by means of the instrument.
Figure 25:
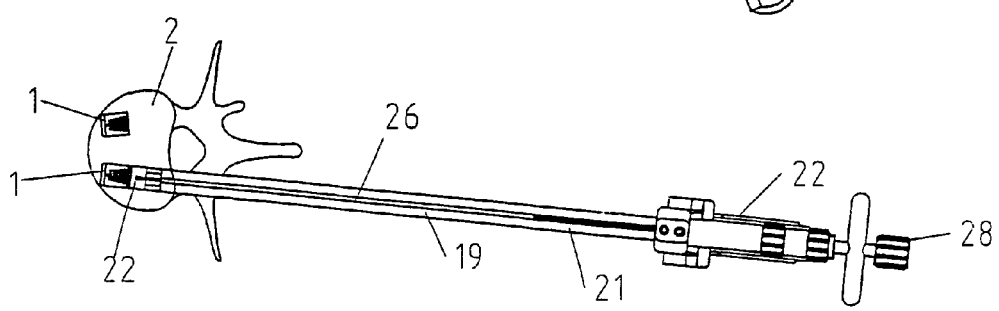
FIG. 25 shows a top view of the implant and the instrument from FIG. 23.
Figures 28, 29:
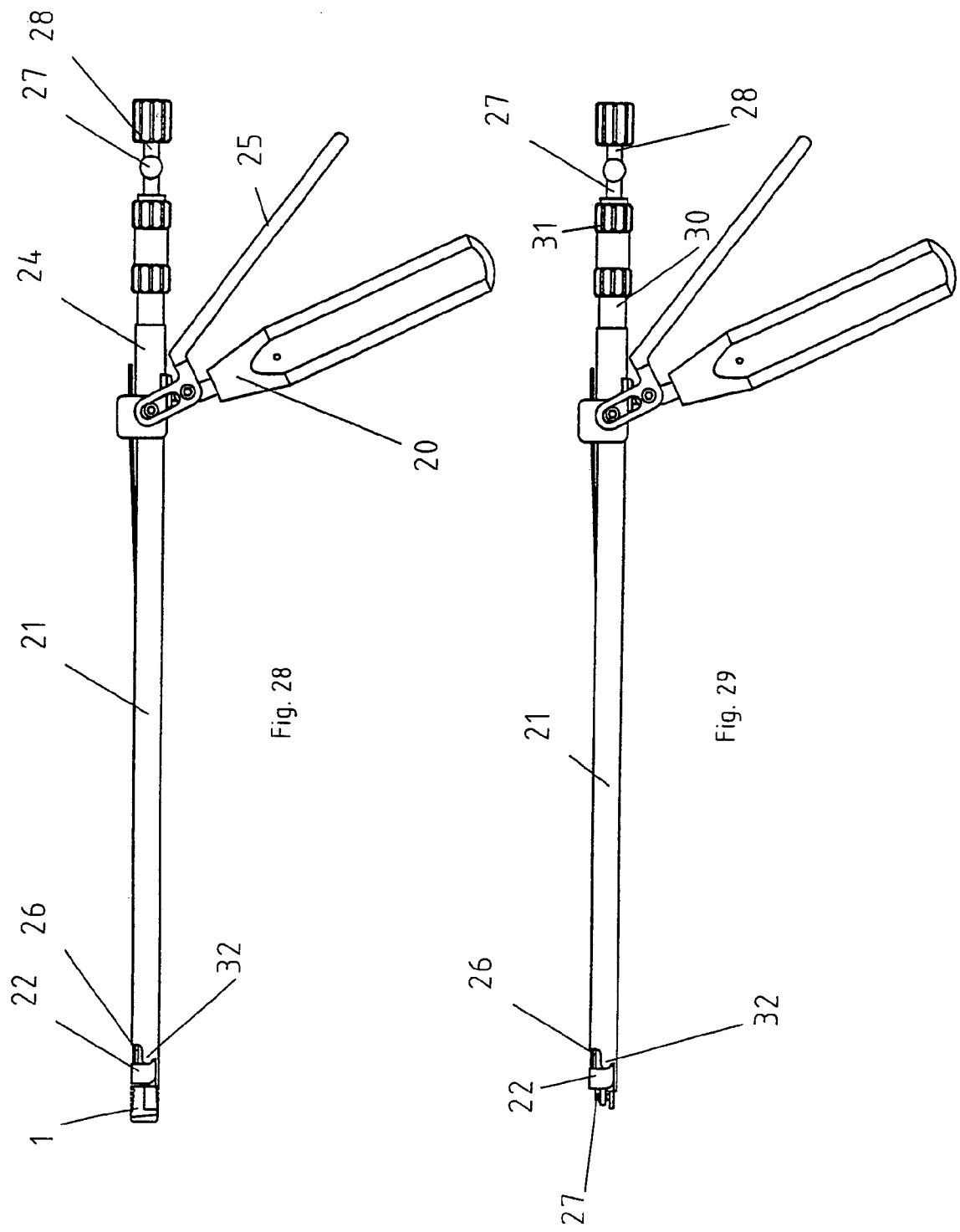
FIG. 28 shows a side view of the implant set onto the instrument.
FIG. 29 shows a representation corresponding to FIG. 28, of an isolated instrument.
Figure 30:
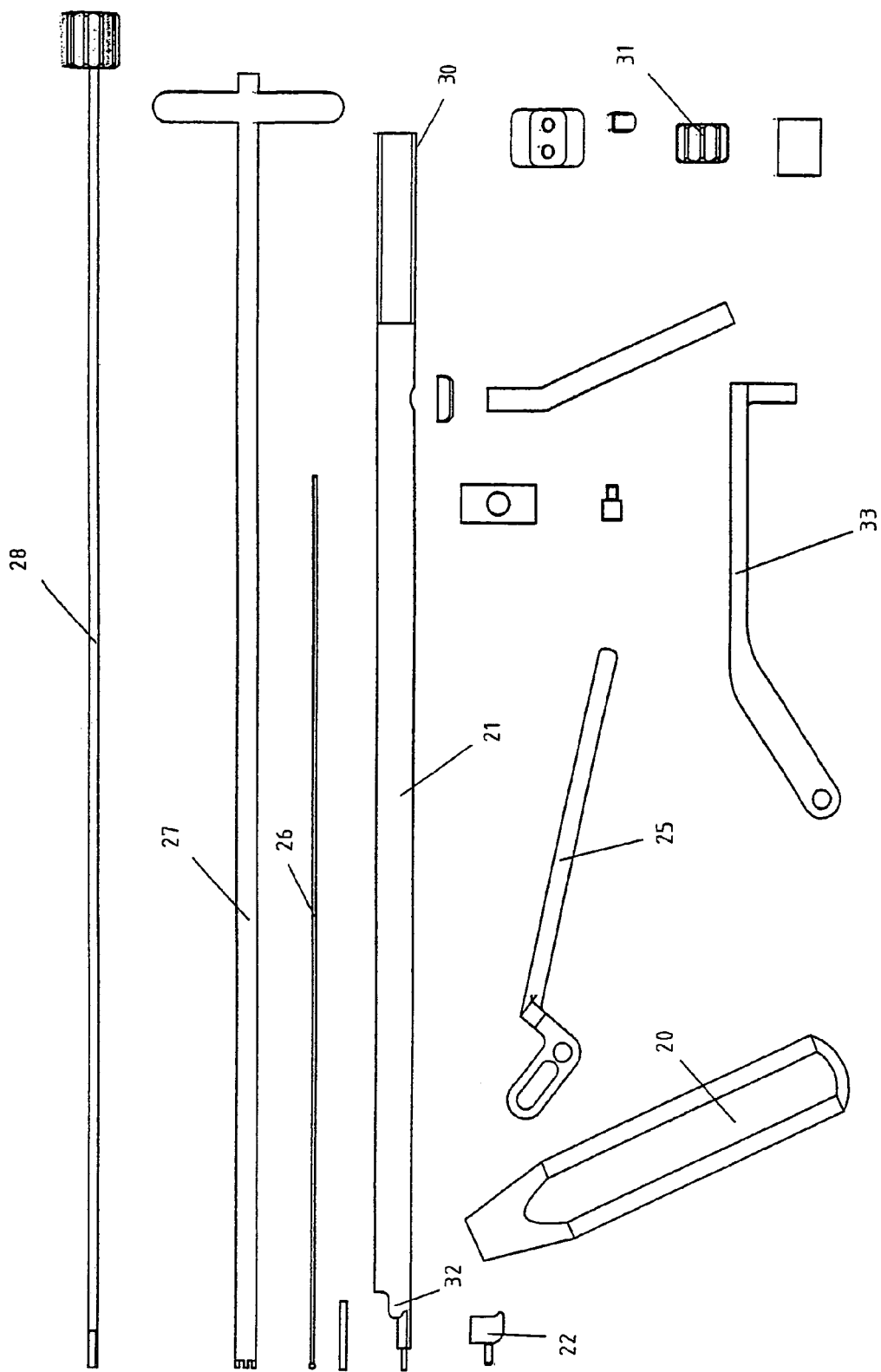
FIG. 30 shows a side view of the individual parts of an instrument taken apart.
Figure 31:
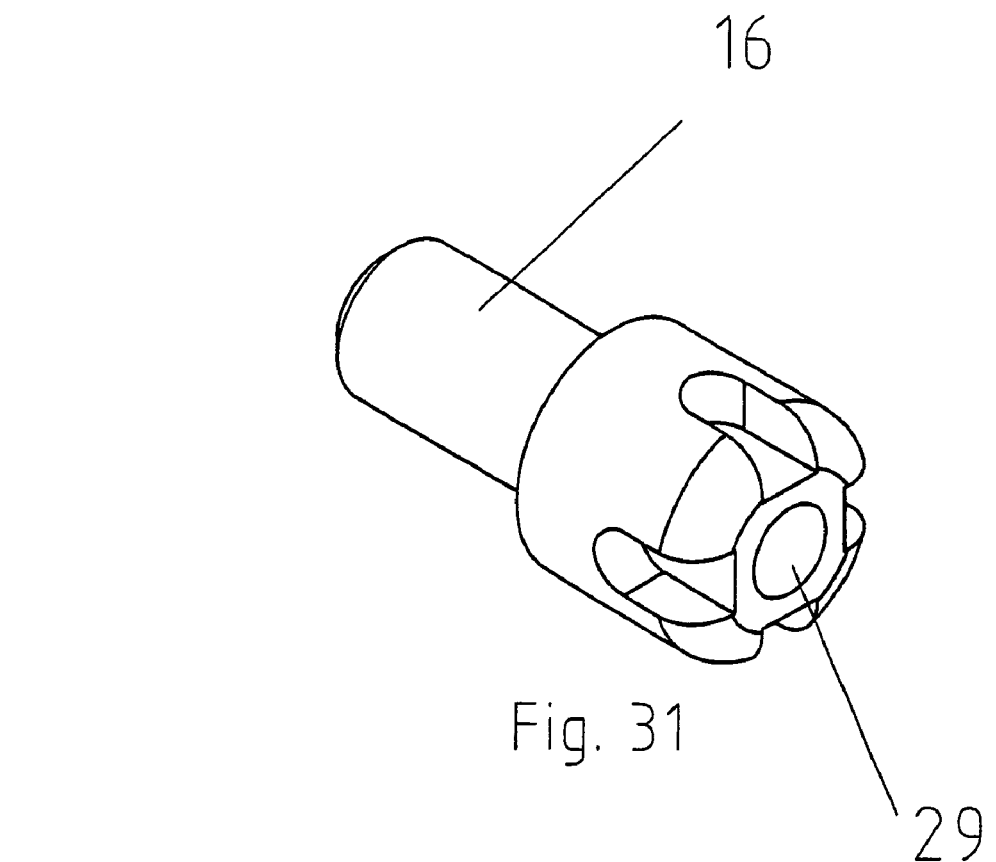
FIG. 31 shows a perspective representation of the locking screw.
Figure 32:
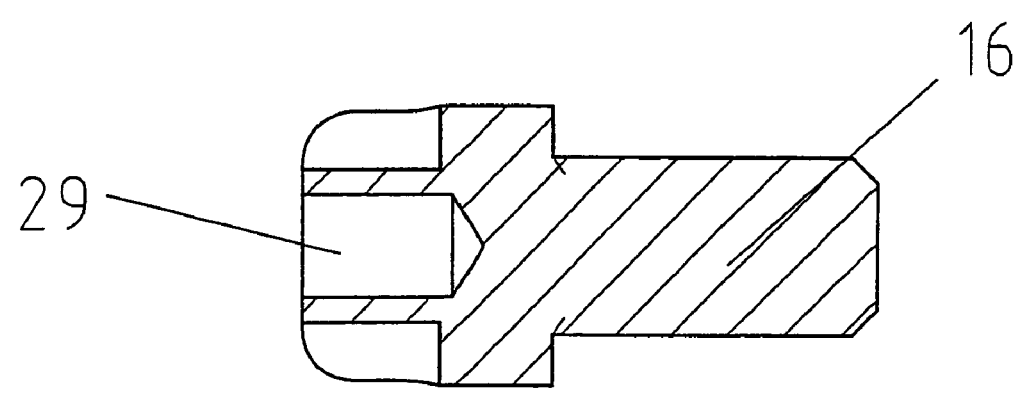
FIG. 32 shows a longitudinal cross-section through the locking screw from FIG. 31.

A plurality of guide grooves 18 is formed in implant opening 17, two of which run along the longitudinal parting between first implant part 3 and second implant part 4, and serve to interact with an instrument 19 which is shown in detail in FIGS. 23 to 30.

FIGS. 1 to 11 and, in particular, the comparison with the implants known from the state of the art, in FIGS. 21 and 22, make the compact construction form of implant 1 according to the invention, with a short length in the axial direction, evident. This results in a varied possibility of use of implant 1, not only from a dorsal or transabdominal direction, but also percutaneously, from a further lateral direction, or with minimal invasiveness, from a ventral direction. The use of implant 1 in pairs as shown in FIG. 20 is preferred, but not necessary, since the ability of implant 1 to withstand stress is so great that if the indication and access are present, a single implant can be used.

Instrument 19 has a hollow rod 21 connected with a handle 20, which rod possesses a pivotable setting element 22 at its front, free end, which element has two pins 23 for insertion into the two guide grooves 18 assigned to the longitudinal parting. A sleeve 24 is connected with a pivoting lever 25 on hollow rod 21, which lever serves to activate a tension piece 26 that engages on setting element 22, for pivoting. Furthermore, a hollow screwdriver 27 is arranged in hollow rod 21, through which screwdriver a threaded pin 28 to be screwed into the threaded bore 29 of the screw head of locking screw 16 passes. A rod thread 30 is formed on the back end of hollow rod 21, with a threaded ring 31 arranged on it, to limit the setting path of sleeve 24. The tension piece 26 engages at the top end of setting element 22, whereby projections 32 are formed on hollow rod 21, in the front region, at the opposite rod walls, which projections define a pivot axis that lies perpendicular to the longitudinal parting of the implant 1. Setting element 22 rests against the projections at a distance from its connection with the tension piece 26. A stirrup 33 is mounted on handle 20, which can be pivoted between a position that limits the axial adjustment path of the threaded pin, and a position that eliminates this limitation.

Accordingly, while only a few embodiments of the present invention have been shown and described, it is obvious that many changes and modifications may be made thereunto without departing from the spirit and scope of the invention.

What is claimed is:

1. An implant for intersomatic fusion of two adjacent vertebrae, comprising:
    a first implant part;
    a second implant part adjustable relative to the first implant part, for the purpose of distraction, wherein the first implant part and the second implant part supplement one another, in a complementary manner, in a non-distracted state, to form a pipe that is divided in a longitudinal direction,
    guide surfaces disposed on the first and second implant parts, said guide surfaces extending radially in a distraction direction and resting against one another; and
    means for fixing the relative position of the guide surfaces in place,
    wherein the guide surface of the first implant part is formed on a face of the first implant part and wherein the guide surface of the second implant part is formed in a radially running slit; and
    wherein the slit widens radially, in a direction toward the first implant part, wherein the second implant part is formed in two parts, a face plate being one of said parts and said face plate being adjustable in an axial direction, and wherein the guide surface of the first implant part is formed on a guide wedge that engages into the slit, said guide wedge having wedge walls that run parallel to walls of the slit.

2. An implant according to claim 1, wherein the guide surface of the second implant part is formed on an inside of the face plate of the second implant part.

3. An implant according to claim 1, wherein an axially running guide groove is formed in the face plate, for interaction with a guide tab formed on the second implant part.

4. An implant according to claim 3, wherein the guide wedge is formed in a circumferential direction, as a ring open on one side, which surrounds a guide tab with a ring opening in the non-distracted state.

5. An implant according to claim 1, wherein the means for fixing the relative position of the guide surfaces comprises an axially running threaded bore on an inward facing side of the face plate, and a ring eye on the second implant part, to hold a locking screw that engages in the threaded bore.

6. An implant according to claim 5, further comprising a threaded bore formed in a free end of the screw head of the locking screw.

7. An implant according to claim 1, wherein an implant opening for access into the interior of the implant is formed on a side opposite the face plate.

8. An implant according to claim 7, wherein a plurality of guide grooves are formed in the implant opening, two of said guide grooves running along a longitudinal parting between the first implant part and the second implant part.

9. An implant according to claim 1, wherein the surfaces of the pipe that lie opposite one another in the distraction direction have gear teeth.

10. An implant according to claim 1, wherein the first implant part and the second implant part are made of surgical steel or titanium.

11. An implant according to claim 1, wherein the means for fixing the relative position of the guide surfaces comprises bone cement introduced between the first implant part and the second implant part.

* * * * *